United States Patent
Rodriguez et al.

(10) Patent No.: US 12,312,389 B2
(45) Date of Patent: *May 27, 2025

(54) METHOD TO PREPARE THERAPEUTICALLY ACTIVE ALDESLEUKIN HIGHLY STABLE IN LIQUID PHARMACEUTICAL COMPOSITIONS

(71) Applicant: Akron BioProducts LLC, Boca Raton, FL (US)

(72) Inventors: Juan Manuel Rodriguez, Buenos Aires (AR); Claudia Zylberberg, Delray Beach, FL (US)

(73) Assignee: Akron BioProducts LLC, Boca Raton, FL (US)

( * ) Notice: Subject to any disclaimer, the term of this patent is extended or adjusted under 35 U.S.C. 154(b) by 944 days.

This patent is subject to a terminal disclaimer.

(21) Appl. No.: 17/118,915

(22) Filed: Dec. 11, 2020

(65) Prior Publication Data

US 2021/0246184 A1 Aug. 12, 2021

Related U.S. Application Data

(63) Continuation-in-part of application No. PCT/US2019/037012, filed on Jun. 13, 2019.

(60) Provisional application No. 62/684,288, filed on Jun. 13, 2018.

(51) Int. Cl.
| | |
|---|---|
| *C07K 1/16* | (2006.01) |
| *A61K 38/20* | (2006.01) |
| *A61K 47/02* | (2006.01) |
| *A61K 47/10* | (2017.01) |
| *A61K 47/20* | (2006.01) |
| *A61K 47/26* | (2006.01) |
| *A61P 35/04* | (2006.01) |
| *C07K 14/55* | (2006.01) |
| *A61K 38/00* | (2006.01) |

(52) U.S. Cl.
CPC .......... *C07K 14/55* (2013.01); *A61K 38/2013* (2013.01); *A61K 47/02* (2013.01); *A61K 47/10* (2013.01); *A61K 47/20* (2013.01); *A61K 47/26* (2013.01); *A61P 35/04* (2018.01); *C07K 1/16* (2013.01); *A61K 38/00* (2013.01)

(58) Field of Classification Search
CPC .......... C07K 1/16; C07K 14/55; A61K 47/02
See application file for complete search history.

(56) References Cited

U.S. PATENT DOCUMENTS

| | | | |
|---|---|---|---|
| 4,604,377 | A | 8/1986 | Fernandes et al. |
| 5,419,899 | A | 5/1995 | Koths et al. |
| 6,955,807 | B1 | 10/2005 | Shanafelt et al. |
| 7,807,142 | B2 | 10/2010 | Chen et al. |
| 10,722,460 | B2 | 7/2020 | Mariau et al. |
| 2018/0303754 | A1 | 10/2018 | Mariau et al. |

FOREIGN PATENT DOCUMENTS

| | | | |
|---|---|---|---|
| EP | 1688146 A1 | | 8/2006 |
| EP | 1688146 B1 | | 7/2007 |
| ES | 2318916 A1 | | 5/2009 |
| GB | 2415904 | * | 2/2005 |
| JP | 2018537423 A | | 12/2018 |
| WO | 2017033025 A1 | | 3/2017 |
| WO | 2017/068031 A1 | | 4/2017 |
| WO | 2019241534 A1 | | 12/2019 |

OTHER PUBLICATIONS

Gorbunoff, Methods in Enzymology, 182: 329-339, (1985).*
Tripathi Nagesh K.: "Production and Purification of Recombinant Proteins from Escherichia coli", Chembioeng Reviews, vol. 3, No. 3, May 12, 2016.
Extended European Search Report mailed on Mar. 17, 2022 in EP 19819023.3.
European Search Report mailed on May 12, 2022 in EP 21213209.6.
Goudy et al.: "Inducible Adeno-Associated Virus-Mediated IL-2 Gene Therapy Prevents Autoimmune Diabetes", The Journal of Immunology, vol. 186, No. 6, Mar. 15, 2011, pp. 3779-3786.
Rosenberg et al., "Regression of Established Pulmonary Metastases and Subcutaneous Tumor Mediated by the Systemic Administration of High-Does Recombinant Interleukin 2." J Exp. Med., 161:5, pp. 1169-1188, 1985.
International Search Report and the Written Opinion dated Nov. 1, 2019 from Corresponding PCT/US2019/037012, 11 pages.
Notice of Reasons for Refusal dated Dec. 20, 2024 in JP Application No. 2020-206270 (machine translation).

* cited by examiner

*Primary Examiner* — Gyan Chandra

(74) *Attorney, Agent, or Firm* — Katten Muchin; ROSENMAN LLP

(57) ABSTRACT

The invention relates to a liquid pharmaceutical composition of aldesleukin/SDS aggregates and its use in the treatment of auto-immune disease, inflammatory disorders and cancer. A method for preparing said composition is also described.

10 Claims, 4 Drawing Sheets

Specification includes a Sequence Listing.

SEQ ID NO: 1:

Pro Thr Ser Ser Ser Thr Lys Lys Thr Gln Leu Gln Leu Glu His Leu Leu Leu Asp Leu Gln Met Ile Leu Asn Gly Ile Asn Asn Tyr Lys Asn Pro Lys Leu Thr Arg Met Leu Thr Phe Lys Phe Tyr Met Pro Lys Lys Ala Thr Glu Leu Lys His Leu Gln Cys Leu Glu Glu Glu Leu Lys Pro Leu Glu Glu Val Leu Asn Leu Ala Gln Ser Lys Asn Phe His Leu Arg Pro Arg Asp Leu Ile Ser Asn Ile Asn Val Ile Val Leu Glu Leu Lys Gly Ser Glu Thr Thr Phe Met Cys Glu Tyr Ala Asp Glu Thr Ala Thr Ile Val Glu Phe Leu Asn Arg Trp Ile Thr Phe Ser Gln Ser Ile Ile Ser Thr Leu Thr

FIG. 1

SEQUENCE LISTING

```
<160> NUMBER OF SEQ ID NOS: 1

<210> SEQ ID NO 1
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
```

-continued

```
                85                  90                  95
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130
```

METHOD TO PREPARE THERAPEUTICALLY ACTIVE ALDESLEUKIN HIGHLY STABLE IN LIQUID PHARMACEUTICAL COMPOSITIONS

CROSS-REFERENCE TO RELATED APPLICATIONS

This application is a continuation-in-part of International Patent Application No. PCT/US19/37012, filed Jun. 13, 2019, which claims the claims the benefit of priority under 35 U.S.C. § 119(e) to U.S. Provisional Application No. 62/684,288, filed on Jun. 13, 2018, which is incorporated herein by reference in its entirety.

INCORPORATION BY REFERENCE OF SEQUENCE LISTING

The contents of the sequence listing text file named "052854-508001WO_Sequence_Listing_txt", which was created on Dec. 11, 2020 and is 1,641 bytes in size, are incorporated herein by reference in its entirety.

FIELD OF THE INVENTION

The invention relates to new pharmaceutical compositions comprising aldesleukin/SDS aggregates stable in solution and their pharmaceutical uses

BACKGROUND

Interleukin 2 (IL-2) is a key cytokine regulating survival, proliferation and differentiation of T cells and NK cells (1). Discovery of these biological activities led to approval for clinical application of IL-2 in cancer immunotherapy for metastatic renal carcinoma in 1994 and for metastatic melanoma in 1998. Afterwards, IL-2 emerged as a reagent to drive in vitro expansion of T lymphocytes extracted from a tumor (tumor infiltrating lymphocytes, TILs) of a patient, that were then transfer back to the patient in order to avoid future cancer development (2). Recently, IL-2 has been also used to expand T cells transduced with antigen-specific T cells receptors (3), or transduced with chimeric antigen receptors (CARs) for cancer treatments (4). A new field of IL-2 medical applications recently emerged as a consequence of the discovery that IL-2 have dual functions in the immune response: a) the well-known activity as activator of the inflammatory response and b) as a down regulator of the inflammatory response inducing the expansion of T regulatory cells (CD4$^+$Foxp3$^+$Treg cells) (5). This seemingly paradoxical duality, can be explain by the existence of two kind of IL-2 receptors with high or low affinities and their particular cellular distribution (5). This IL-2 duality resulted in opposing therapies as follows: a) use of IL-2 in high doses to stimulate the immune response like in the original treatments of cancer, and b) use of IL-2 in low doses to depress excessive or aberrant immune response like in the treatment of autoimmune or inflammatory disorders.

Most (if not all) of the current clinical applications of IL-2 are carried out using a recombinant mutated version of natural IL-2 named aldesleukin (des-ala-2ser125) (PROLEUKIN™). U.S. Pat. No. 4,604,377 teaches how to prepared a pharmaceutical composition of recombinant IL-2 (including aldesleukin) consistent in a sterile, stable lyophilized formulation in which the recombinant IL-2 is admixed with a water soluble carrier such as mannitol that provides bulk, and sufficient amount of sodium dodecyl sulfate to ensure the solubility of the recombinant IL-2 in water. The formulation is suitable for reconstitution in aqueous injections for parenteral administration stable and well tolerated in human patients. On the other hand, a detailed description of the process by which the PROLEUKIN™ product is prepared has been more recently disclosed in the European patent EP 1,688,146 B.

SUMMARY

One aspect of the present invention is a method to prepare aldesleukin highly stable in liquid pharmaceutical compositions for parenteral administration to a patient in need of an IL-2 immunotherapy, comprising, in general, the following steps: a) Fermentation of an E. coli strain transfected with an expression vector engineered to highly express the aldesleukin gene, b) Bacterial disruption, c) Collection of Inclusion bodies containing aldesleukin aggregates, d) Dissolution of the aldesleukin aggregates using SDS detergent, e) Oxidation with an oxidizing compound e.g. cupric chloride, f) Ceramic hydroxyapatite chromatography, g) Dilution with an organic nitrile, e.g. acetonitrile, h) C4 column HPLC chromatography, i) Diafiltration and j) Filter sterilization.

A second aspect of the present invention is a composition of aldesleukin in a pharmaceutical for parenteral administration to a patient in need of IL-2 immunotherapy, in which the aldesleukin has been prepared using the production method of the invention that ensures that the aldesleukin is stable in a pharmaceutical liquid composition for at least a year. With the composition of aldesleukin of the invention it is possible to prepare a pharmaceutical product consistent in one or more pre-filled syringes, each one containing a dose suitable for a given treatment, packaged in a box. This product would not need any manipulation previous to the injection into the patient, avoiding for example microbial or other possible contaminations. On the other hand, the stable liquid aldesleukin preparation of the invention could be advantageously introduced and homogeneously distributed in parenteral solutions commonly used in medicine for infusion, transfusion or clinical nutrition. Lately, treatments consisting in a given drug plus aldesleukin has been developed (e.g. CEPLENE™ (histamine dihydrochloride) is administered in conjunction with low dose of proleukin for maintenance of first remission in patients with Acute Myeloid Leukemia). For such treatments, the stable liquid aldesleukin preparation of the invention may serve as the base to elaborate a unique combined preparation or a combined kit. Proleukin has already been also used to induce in vitro proliferation of susceptible cells to be used in cell therapy procedures (5). For these procedures, the stable liquid aldesleukin of the invention, formulated in low concentrations, can be very advantageous in order to avoid manipulations that can result in microbial contamination and also in order to obtain a rapid and homogeneous distribution of aldesleukin in the cell culture.

A third aspect of the present invention is a composition of aldesleukin in a suitable aqueous vehicle for use as ancillary material in any ex-vivo cell therapy procedure involving cells expressing an IL-2 receptor in their membrane. Examples of these cells already known in the art are Natural Killer (NK) and different types of Lymphocytes, such as T cells, CAR-T cells, CAR-NK cells and the like.

These are only few examples, however a person in the art, can easily imagine other applications of the stable liquid aldesleukin preparation of the disclosure.

A fourth aspect of the present disclosure, comprises a pharmaceutical composition comprising an IL-2 molecule embodied herein e.g. SEQ ID NO: 1, in a range from about 0.001 mg/ml to about 3 mg/ml. In certain embodiments, the pharmaceutical composition comprises sodium dodecyl sulfate (SDS) in a range from about 0.05 mg/ml to about 20 mg/ml, osmolytes, a pH 7-8 phosphate buffer or combinations thereof.

In a fifth aspect, a pharmaceutical composition comprises IL-2, SDS, an osmolytes, a pH 7-8 phosphate buffer or combinations thereof. In certain embodiments, the pharmaceutical composition consists of IL-2, sodium dodecyl sulfate (SDS) in a range from about 0.05 mg/ml to about 20 mg/ml, osmolytes and a pH 7-8 phosphate buffer.

In certain embodiments the osmolytes comprise sodium chloride, mannitol, sorbitol, xylitol or combinations thereof.

The IL-2 molecules herein include IL-2 variants of the present disclosure comprising an amino acid sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the IL-2 amino acid sequence (SEQ ID NO: 1). These include IL-2 variants that comprise an amino acid sequence having an N88R mutation that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the wild-type IL-2 amino acid sequence (i.e. SEQ ID NO: 1). Embodiments also include IL-2 variants that preferentially stimulate Treg cells and comprise an amino acid sequence having N88R and C125S mutations that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% sequence identity to the wild-type IL-2 amino acid sequence (SEQ ID NO: 1). Embodiments also include IL-2 variants that preferentially stimulate Treg cells and comprise an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the wild-type IL-2 amino acid sequence (SEQ ID NO: 1).

BRIEF DESCRIPTION OF THE FIGURES

FIG. 1: Amino acid sequence of the recombinant human interleukin 2 (Aldesleukin) (SEQ ID NO: 1).

DETAILED DESCRIPTION

Figure 2:
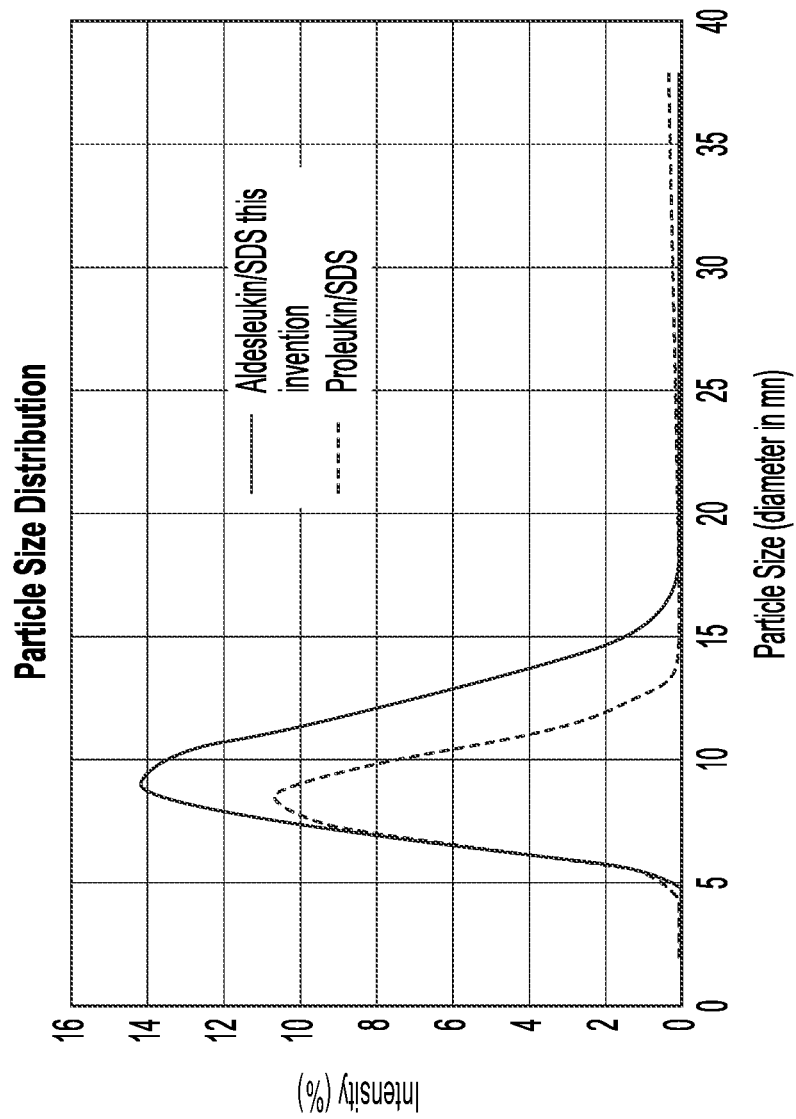
FIG. 2: Comparison of the aldesleukin/SDS particle size range, as measured by dynamic light scattering, between PROLEUKIN™ and the aldesleukin prepared by the method of this invention.

Embodiments of the disclosure are directed to a highly stable IL-2 in a liquid formulation and methods of producing the stable IL-2.

Definitions

The terminology used herein is for the purpose of describing particular embodiments only and is not intended to be limiting of the disclosure. Unless specifically defined otherwise, all technical and scientific terms used herein shall be taken to have the same meaning as commonly understood by one of ordinary skill in the art (e.g., in cell culture, molecular genetics, and biochemistry).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

The term "a suitable aqueous pharmaceutical composition" means a sterile water containing composition which can include one or more chemical compounds, such as for example, PBS, sodium dodecyl sulfate (SDS), osmolytes, cell culture media, cryopreservative compositions, and the like. The aqueous composition can further comprise: a salt, an acid, a base, a non-ionizable salt, a soluble salt, a partially-soluble salt, a sugar, a fat, an organic liquid, an organic solvent, an organic solid, a pharmaceutical excipient, an amino acid, an organic acid, an organic base, an alcohol, a ketone, an aldehyde, a carboxylic acid, an ether, an amine, an amide, an ester, an alkyl halide, an aromatic compound, a cyclic compound, a heterocyclic compound, a polypeptide, an oligosaccharide, a carbohydrate, an oxide, a peroxide, a carbonyl, an alkene, an alkyne, a lipid, an adjuvant, an enzyme, a protein, a nucleic acid, a cation(s), an anion(s), a hydrocarbon, an oil, a wax, a starch, a chelator, a pH buffer, a reducing agent, an oxidizing agent, a surfactant, a catalyst, an inorganic nanoparticle, an organic nanoparticle and any combinations thereof. Examples of cations include, aluminum ion, ammonium ion, antimony ion, barium ion, bismuth ion, boron ion, calcium ion, cerium ion, cesium cation, chromium ion, cobalt ion, copper ion, dysprosium ion, erbium ion, europium ion, gadolinium ion, gallium ion, germanium ion, gold ion, hafnium ion, holmium ion, indium ion, iridium ion, iron ion, lanthanum ion, lithium ion, lutetium ion, magnesium ion, manganese ion, molybdenum ion, neodymium ion, nickel ion, niobium ion, osmium ion, palladium ion, phosphorus ion, platinum ion, potassium ion, praseodymium ion, rhenium ion, rhodium ion, rubidium ion, ruthenium ion, samarium ion, scandium ion, selenium ion, silicon ion, silver ion, sodium ion, strontium ion, sulfate ion, tantalum ion, tellurium ion, terbium ion, thulium ion, tin ion, titanium ion, tungsten ion, vanadium ion, ytterbium ion, yttrium ion, zinc ion, zirconium ion, and any combinations thereof. Examples of anions include a bromide, a chloride, a fluoride, an iodide, a nitrate, a nitrite, a sulfate, a sulfite, a phosphate, a hydrogen phosphate, a dihydrogen phosphate, a Good's buffer anion, a carbonate, a bicarbonate, an EDTA anion, a citrate, a carboxylic acid anion, an inorganic anion, an organic anion any combinations thereof.

A "biological medium" as used herein, is any type of medium that is used to grow, culture and maintain organs, tissues, cells etc., in vitro. A biological medium also encompasses any biocompatible agent, any pharmaceutical excipient, pharmaceutically and physiologically acceptable fluids such as water, physiological saline, balanced salt solutions, aqueous dextrose, glycerol or the like as a vehicle, tissue or organ culture media, any agent that can be administered in vivo to a subject, any agent that can be used in assays or for diluting or maintaining a biological sample, e.g. nucleic acids, peptides etc.

As used herein, the term "cell" includes prokaryotic and eukaryotic cells. In one embodiment, a cell of the disclosure is a bacterial cell. In another embodiment, a cell of the disclosure is a fungal cell, such as a yeast cell. In another embodiment, a cell of the disclosure is a vertebrate cell, e.g., an avian or mammalian cell. In a preferred embodiment, a cell of the disclosure is a murine or human cell. As used herein, the term "engineered" (as in an engineered cell) refers to a cell into which a nucleic acid molecule e.g., encoding an IL-2 protein (e.g., a spliced and/or unspliced form of IL-2) or fragments thereof, has been introduced.

As used herein, the term "cell free composition" refers to an isolated composition, which does not contain intact cells. Examples of cell free compositions include cell extracts and compositions containing isolated proteins.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "expression vector" refers to a vector containing a nucleic acid sequence coding for at least part of a gene product capable of being transcribed. In some cases, when the transcription product is an mRNA molecule, this is in turn translated into a protein, polypeptide, or peptide.

As used herein, the term human recombinant IL-2 (rhIL-2) is an unglycosylated protein produced by a microorganism that has been transfected with the human IL-2 codifying DNA sequence or a non-extensive modification of it. In fact, the IL-2 human recombinant version most used in clinical practices is modified version of the natural human IL-2 amino acid sequence, named aldesleukin (PROLEUKIN™) having the following modifications: a) aldesleukin has no the N-terminal alanine present in natural IL-2 b) aldesleukin has serine substituted for cysteine at amino acid position 125. Aldesleukin amino acid sequence is shown in FIG. 1. Construction of the aldesleukin gene is described in U.S. Pat. No. 4,518,584A and related non-US patents. The United States FDA has approved aldesleukin (PROLEUKIN™) for use in the treatment of adults with metastatic renal cell carcinoma and metastatic melanoma. PROLEUKIN™ is supplied as a sterile, white to off-white, lyophilized cake in 20 single-use vials intended for intravenous administration. When reconstituted with 1.2 mL Sterile water for Injection, USP, each mL contains 18 million International Units (1.1 mg) PROLEUKIN™, 50 mg mannitol, and 0.18 mg sodium dodecyl sulfate, buffered with approximately 0.17 mg monobasic and 0.89 mg dibasic sodium phosphate to a pH of 7.5 (range 7.2 to 7.8). Reconstituted or diluted PROLEUKIN™ is stable for up to 48 hours at refrigerated and room temperatures, 2° to 25° C. (36° to 77° F.) as stated in the Reconstitution and Dilution Directions of the "PROLEUKIN™ (aldesleukin) injection label—FDA" (Reference ID: 3165255).

As used herein, the term "interleukin 2" (IL-2) denotes a cytokine that regulates the activities of white blood cells (mainly lymphocytes). This cytokine is part of the immune response to microbial infections and exercise its effects by binding to specific receptors present on the surface of lymphocytes. Further information about IL-2 can be found in its "GeneCard" (accession number GC04M123831). Other accession numbers include: HGNC: 6001 Entrez Gene: 3558 Ensembl: ENSG00000109471 OMIM: 147680 UniProtKB: P60568. IL-2 proteins include native IL-2 proteins, as well as variant IL-2 proteins. A "native" or "wild type" IL-2 sequence, as used herein, refers to a human IL-2 sequence (e.g., Accession No. NP 000577.2), whether purified from natural sources or made using recombinant techniques. In some embodiments, a wild type IL-2 sequence includes the PROLEUKIN™ (aldesleukin) sequence: (SEQ ID NO: 1) PTSSSTKKTQ LQLEHLLLDL QMILNGINNY KNPKLTRMLT FKFYMPKKAT ELKHLQCLEE ELKPLEEVLN LAQSKNFHLR PRDLISNINV IVLELKGSET TFMCEYADET ATIVEFLNRW ITFSQSIIST LT Human IL-2 sequence (e.g., Accession No. NP 000577.2) (SEQ ID NO: 2): MYRMQLLSCI ALSLALVTNS APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT.

As used herein, the term "kit" refers to any delivery system for delivering materials. Inclusive of the term "kits" are kits for both research and clinical applications. In the context of reaction assays, such delivery systems include systems that allow for the storage, transport, or delivery of reaction reagents (e.g., cytokines, oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides or liposomes. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used in this specification and the appended claims, the term "or" is generally employed in its sense including "and/or" unless the content clearly dictates otherwise.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, "stable" or "highly stable" refers to the activity and/or the integrity of the molecule, e.g. IL-2, in the formulations embodied herein, over extended periods of time, as evaluated by biological activity in vitro, structural studies in vitro and therapeutic activity in vivo. The activity of the IL-2 can be measured by any standard assay. The activity before storage and after long-term storage, e.g. at least one year, can be compared. Highly stable IL-2 would have the same or slightly less activity as compared to the activity at the time of IL-2 when first formulated.

Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Methods of Producing Stable IL-2 Formulations

The disclosure is based in part on a novel method for preparing aldesleukin, which results in a product fulfilling all the structural and biological characteristics of PROLEUKIN™ but that surprisingly is very stable (at least one year) in solution as evaluated by biological activity "in vitro", structural studies "in vitro" and therapeutic activity "in vivo". An exemplary method to prepare aldesleukin largely stable in solution comprises the following steps:

a) Fermentation of an *E. coli* strain transfected with an expression vector engineered to highly express the aldesleukin gene. Bacteria are preferred microorganisms for producing IL-2 and among bacteria *E. coli* strains are the most preferred. *Escherichia coli* B serves as a research model and also for protein expression in life science laboratories and in the biotech industry. Characteristics such as protease deficiency, low acetate production at a high level of glucose, and enhanced permeability (probably due to a simple cell surface) make *E. coli* B a desirable host for the production of genetically engineered proteins. Differences between B strains and K12 include the absence of flagellar component genes, the DNA cytosine methylase dcm, and ompT in BL21(DE3). B strains may have an additional type II secretion system not found in K12. BL21(DE3) also carries a DE3 recombinant phage harboring the T7 RNA polymerase gene that can direct high-level expression of cloned genes under the control of the T7 promoter. Typical *E. coli* strains used for recombinant protein expression are: BL21 (a B *E. coli* strain that protects target protein from lon and ompT proteases) and their derivatives such as: Lysogenic DE3 (based on T7 polymerase), pLysS, pLysE (express T7 lysozyme reducing basal expression of target genes), Origami (allows disulfide bond formation in *E. coli* cytoplasm), Rosetta (enhances expression of proteins that contain codons rarely used in *E. coli*). Similar versions exists under the K12 *E. coli* genetic background. Typical plasmid vectors for high expression of recombinant proteins in *E. coli* are: pET series based on pBR322 origin and T7/lac promoters; pBad with araBAD promoter and pUC origin; pGEX with tac promoter and pBR322 origin also. Combination of fusion tags sequences, protease cleavage sites, selection markers and strain compatibility are source for the most usual list of high expression plasmid variants.

Expression vectors are commercially available and a DNA sequence coding for the aldesleukin amino-acid sequence is inserted into the vector. The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell. In a another embodiment, the cell is a human cell. The cells of the disclosure can express endogenous IL-2 or fragments thereof, or can be engineered to do so. For example, a cell that has been engineered to express the IL-2 or fragments thereof can be produced by introducing into the cell an expression vector encoding the protein.

In certain embodiments, the cell is an *E. coli* cell. Different *E. coli* strains can be transfected in order to obtain optimal aldesleukin production.

a) Aldesleukin producing bacteria can be cultured in a suitable growth medium. For example, the medium may contain each 9 liters, 216 gr of Yeast Extract, 108 gr of Soy Peptone, 113 of gr $K_2HPO_4$, 20.8 gr $KH_2PO_4$, 36 ml of Glycerol and 4 ml of Antifoam (2% v/v). Fermentation conditions may be: Temperature: 37° C.±0.5° C., agitation: 350 rpm±10 rpm, air flow: 9 L/min±1 L/min, pO2: set point 40%, agitation cascade: between 21% and 36% running between 350 rpm and 440 rpm, pH between 6.95 and 7.5 and inlet air pressure at 2 bar before starting Oxygen flow. After this, a feeding procedure should be followed. For example, feeding with a glucose solution 40% p/v by drip, to maintain a concentration of 0.1%. Once the OD600 reaches 5 to 10, an appropriated inducer such as Isopropil-β-D-1-tiogalactopiranósido (IPTG) should be added to reach an operative concentration. At this point, the feeding with Glucose may be reduced to keep a glucose concentration of about 0.01%. Fermentation can be stop usually about 18 to 24 hours after inoculation. After fermentation, bacteria can be concentrated 5 to 7 times by centrifugation or tangential filtration and processed immediately or preserved at 2-8° C. (no more than 24 hours) or preserved at −20° C. (for more than 24 hours).

b) After culture, aldesleukin is inside the bacteria, predominantly in the form aggregates named inclusion bodies (Ib). These Ib can be isolated by disruption of bacteria (for example by sonication). For this, bacteria could be suspended in purified water at temperature between 17 and 22° C. before starting the disruption process. After this, the suspension could be circulated 2-3 times for the disruptor at a pressure of about 1400 bar. The lysate should be processed immediately or preserved at −20° C. The Ib are separated of other components of the lysate by centrifugation or tangential filtration and washed. The final buffer for the Ib washing may be TE (10 mM Tris-HCl, 1 mM disodium EDTA, pH 8.0). The Ib preparation should be stored at −20° C. until further processing. The Ib are then suspended in a buffer containing 10 mM sodium Phosphate, 1% SDS, pH8.0 and stirred for 1 hour. Then, an oxidation solution of cupric chloride is added to reach 100 µM final concentration and stirring should continue for 2 more hours. After this EDTA should be add to reach a 100 µM final concentration. The Mixture should be store at 2-8° C. until used in the downstream process.

c) The first chromatography is carried out using a ceramic hydroxyapatite (Type I 80 µm Bio-Rad) column. The aldesleukin preparation is loaded, washed with a solution 100 mM sodium phosphate, 0.3% SDS, pH 6.5 and eluted with a solution 250 mM sodium phosphate, 0.3%, pH 6.5.

d) The second chromatography is carried out using an HPLC C4 column. The solution containing the aldesleukin recovered from the first chromatography is mixed with acetonitrile (9 parts of the chromatography I pool elution and one part of Acetonitrile). After loaded aldesleukin is eluted using a gradient of Acetonitrile. Fractions containing aldesleukin are collected in a solution containing 73 mM sodium phosphate, 0.3% SDS, pH 7.4.

e) The last step in aldesleukin purification is a diafiltration using 5 kD cassettes. Aldesleukin is equilibrated using a pH 7-8 phosphate buffer. The buffer may contain up to 0.1% SDS and up to 50 mg/mL mannitol, depending on the concentration of IL-2 of the solution obtained before this step.

Surprisingly it was found that the aldesleukin obtained by the production method of the disclosure does not need to be lyophilized as described in EP 1 688 146 B1 to be stabilized, since it is stable in solution for at least one year as described in examples 3 and 4. There are several differences between the process disclosed in EP 1 688 146 B1 and our manufacturing process. Some of the main differences are:

After dissolution of inclusion bodies, no precipitation step is needed for the purification of IL-2 in the method disclosed herein which is in contrast to EP 1 688 146 B1.

Only two chromatographic steps are used in the process disclosed herein, whereas the process disclosed in EP 1 688 146 B1 includes three chromatographic steps.

Hydroxyapatite is used as the first chromatographic step, but this stationary phase is never used in EP 1 688 146 B1.

The method disclosed herein does not require precipitation of IL-2 therefore there is no need to re-solubilize it using high levels of SDS.

According to the dynamic light scattering assays shown in examples 3 and 4, the aldesleukin/SDS aggregates obtained by the production method of the disclosure have an extended size range between 4 and 18 nm with a peak at about 8 nm. Even though reconstituted PROLEUKIN™ also shows a similar distribution curve, the area under this curve is clearly lower than the area under the curve of the aldesleukin/SDS particles prepared by the method of the disclosure. Since the protein mass used in both cases is the same, this result suggests that upon reconstitution, part of the PROLEUKIN™ may remain as large aggregates. In fact, in order to measure the full activity of PROLEUKIN™, it has been reported that the lyophilized preparation should be suspended in an SDS solution to avoid aggregate formation (6).

WO 2017068031 A1 describes a liquid pharmaceutical composition suitable for injection to a patient, consisting essentially of interleukin-2 at a concentration of 0.1 to 20 million IU/mL can be obtained. This composition contains an anionic surfactant, such as sodium dodecyl sulfate (SDS) that may be present at a concentration of about 0.05 to 0.5 mg/ml. This composition is not taught to be suitable for ex vivo use. Moreover, there is neither a reference regarding the formation of microaggregates, nor a description of how SDS is added to the composition to allow the formation of these microaggregates in the liquid compositions disclosed in WO 2017068031. Therefore, liquid compositions disclosed in WO 2017068031 are different from the liquid compositions of the invention, in that these do contain the microaggregates taught to be therapeutically relevant by EP 1 688 146 B1. Examples 3 clearly show the formation of microaggregates in the compositions of the invention, whereas example 4 shows the stability of a liquid composition of IL-2 obtained by the process of the disclosure. Example 5 show the biological activity of this composition in the expansion of T cells, as a particular case of the ex-vivo biological activity of the disclosure on cells expressing IL-2 receptors in their membranes.

The following examples further illustrates the disclosure. These examples are not intended to limit the invention in any manner.

EXAMPLES

Example 1: Amino Acid Sequence of the Aldesleukin Obtained by the Production Method of the Invention The amino acid sequence of the aldesleukin obtained by the production method of the invention was deduced by DNA sequencing of the aldesleukin gene present in the expression plasmid used in the method. FIG. 1 shows the obtained amino acid sequence.

Example 2: Specific Activity of the Aldesleukin SDS Aggregates Obtained by the Production Method of the Invention The biological activity of the aldesleukin/SDS aggregates obtained by the production method of the invention was determined by the proliferation of the HT-2 cell line assay. The specific activity of 20 independent lots was in the range of 16.6-19.5 million IU/mg calibrated with the WHO International Standard for INTERLEUKIN 2 (Human, rDNA derived) NIBSC code: 86/500. This range of specific activity is similar to the declared specific activity of the aldesleukin/SDS aggregates prepared according to EP 1 688 146 B1.

Example 3: Comparative Size, Measured by Dynamic Light Scattering, of the SDS/Proleukin Aggregates Obtained after Reconstitution from the Lyophilized Commercial Preparation and the SDS Aldesleukin Aggregates Obtained Using the Method of the Invention A liquid preparation containing 2.2 mg/mL aldesleukin was obtained with the method of the invention with the following final composition: 0.44 mg/ml SDS, 50 mg/ml mannitol, 1.19 mg/ml disodium phosphate, 0.26 mg/ml monosodium di-hydrated phosphate, pH 7.5. This preparation was analyzed by dynamic light scattering to determine the size and polydispersity of the aldesleukin/SDS aggregates using a Zetasizer Nano ZS and the Zeta Nano Series software (Malvern Instruments, Germany). 100 μL sample was diluted in 1 mL pure water and measured at 25° C. five times for 30 sec with 30 sec equilibration time between measurements. Particle size is expressed as the hydrodynamic diameter in nm. FIG. 2 shows dynamic light scattering patterns for the SDS/aldesleukin aggregates obtained using the method of the invention and for PROLEUKIN™ after reconstitution from the lyophilized commercial preparation. The aldesleukin/SDS aggregates obtained by the production method of the invention display an extended size range between 4 and 18 nm with a peak at about 8 nm. PROLEUKIN™ also shows a similar distribution curve. However, the area under this curve is clearly lower than the area under the curve of the aldesleukin/SDS particles prepared by the method of the invention. Since the protein mass used in both analyzed samples was the same, this result suggests that upon reconstitution, part of the PROLEUKIN™ may remain as large aggregates not amenable to be studied with the used technique.

Example 4: Stability of the Aldesleukin Obtained by the Production Method of the Invention A liquid preparation containing 2.2 mg/mL aldesleukin was obtained with the method of the invention with the following final composition: 0.44 mg/ml SDS, 50 mg/ml mannitol, 1.19 mg/ml disodium phosphate, 0.26 mg/ml monosodium di-hydrated phosphate, pH 7.5. This preparation was stored at 2-8° C.

Table 1 shows the activity changes in specific activity with the storage time at 2-8° C. Besides the specific activity, in each sample the following characteristics were assayed: visual observation for anomalies, pH, volume, Western Blot, SDS PAGE (reducing and non-reducing conditions), Lowry, endotoxin contamination (LAL test) and sterility. At all measured times, these assays resulted normal.

TABLE 1

Specific activity of the soluble aldesleukin/SDS aggregates obtained by the method of this invention (SDS concentration)

| Time (months) | 0 | 3 | 6 | 9 | 12 |
|---|---|---|---|---|---|
| Specific activity (IU/mg) | 18.8 | 17.1 | 16.5 | 16.9 | 17.4 |

Figure 3A:
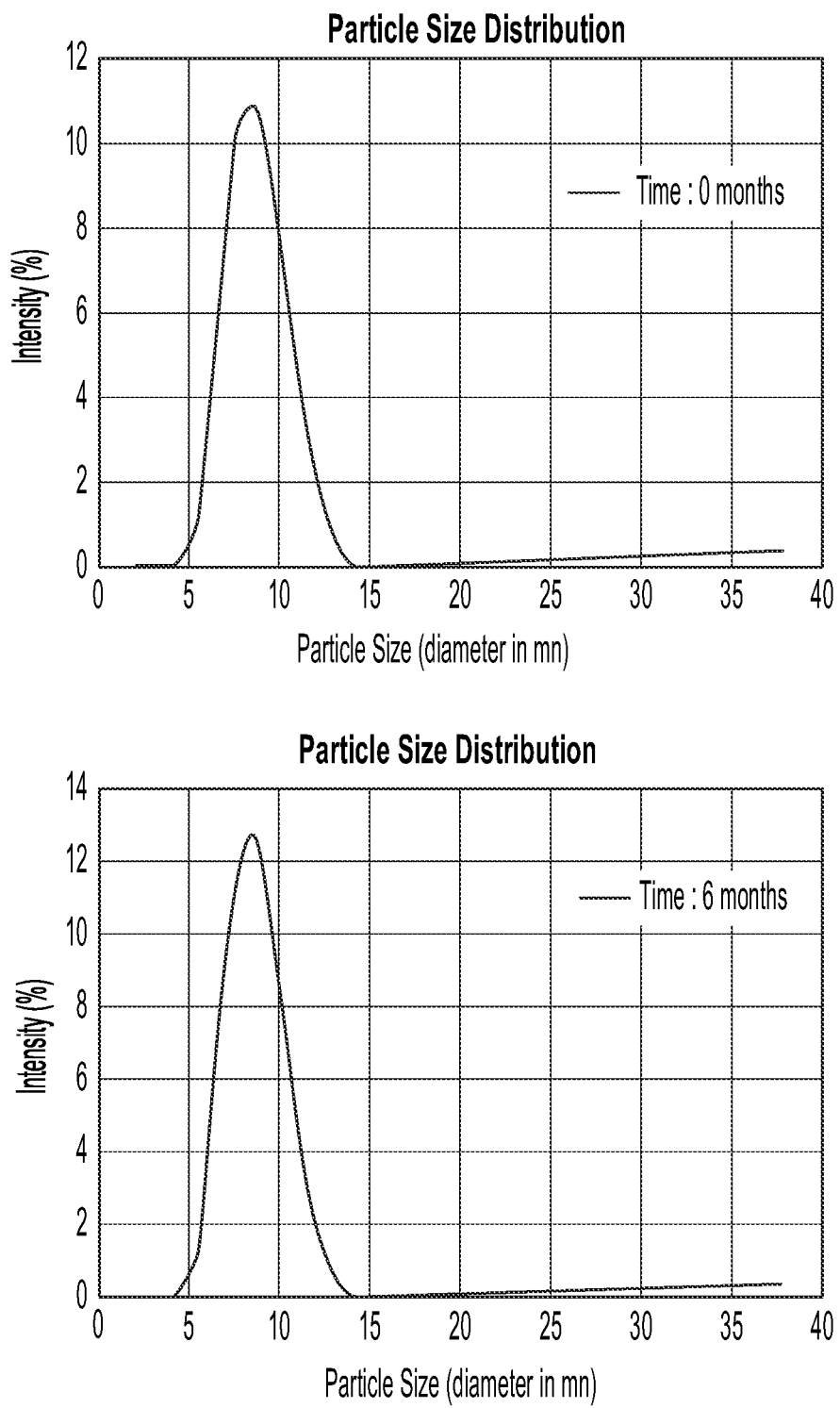
FIGS. 3A and 3B: Aldesleukin/SDS particle size range of the aldesleukin prepared by the method of this invention after 0, 6 or 12 month storage at 0-8° C.
Figure 3B:
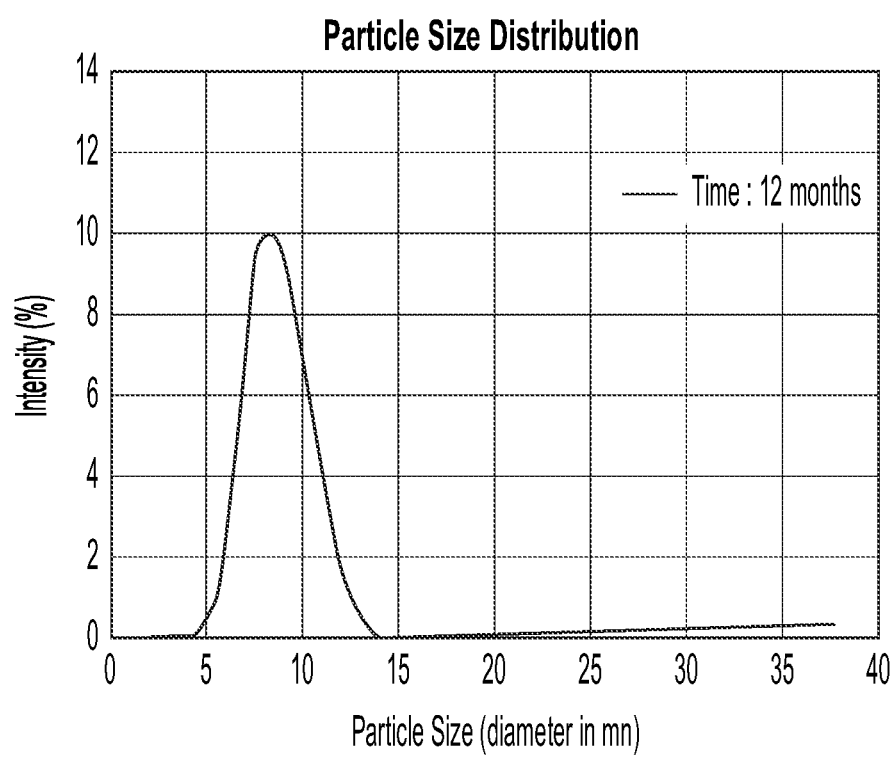

Furthermore, FIG. 3 shows that the size distribution of the aldesleukin/SDS aggregates, as measured by dynamic light scattering, is well preserved in the aldesleukin liquid composition of the invention after 6 or 12 months storage at 2-8° C.

Example 5: Regulatory T Cells (Treg) Expansion in Human Peripheral Mononuclear Blood Cells (PMBC) Incubated with the SDS/Aldesleukin Obtained by the Production Method of the Invention Treg cells were recovered from human PMBC using the DYNABEADS™ Regulatory $CD4^+/CD25^+$ T Cell Kit (ThermoFisher Scientific). Aldesleukin/SDS capacity to induce Treg proliferation was evaluated using the CD3/CD28 DYNABEADS® Human Treg Expander ((ThermoFisher Scientific) protocol. 500 IU of the aldesleukin preparations were used for Treg expansion. After 7 days expansion Tregs were counted. Expansion was 76-125 times for both, the aldesleukin/SDS obtained using the method of the invention or the method fully disclosed in EP1 688 146 B1.

Example 6: Therapeutic Activity of the Aldesleukin SDS Aggregates Obtained Using the Production Method of the Invention A pulmonary metastasis model using B16F10 tumor cells as described (7), was used in order to compare the therapeutic efficiency of the aggregates of aldesleukin prepared by the method of this invention and the aldesleukin/SDS aggregates of PROLEUKIN™. Eight week old female C57BL/6 mice were intravenously injected into the tail vein with 0.5 ml of a cell suspension containing $2 \times 10^5$ B16 cells. After this, mice were separated in three groups of ten mice each. Group 1 mice received a 7.0 mg/Kg dose of PROLEUKIN™, daily from days 3 to 10. Group 2 mice received a 7.0 mg/Kg dose of the micro-aggregates of aldesleukin prepared by the method of this invention, daily from days 3 to 10. Group 3 mice received vehicle daily from days 3 to 10. Mice were euthanized on day 16 after tumor inoculation and lung metastases counted as described (7). Table 2 shows that the median number of metastases observed with the micro-aggregates prepared by the method of this invention was 4.3 (range 1-12), compared to 5.5 (range 3-22) with PROLEUKIN™, being this difference not significant.

TABLE 2

Therapeutic activity of the aldesleukin/SDS aggregates obtained using the production method of the invention

| Treatment | metastases (mean) | range |
|---|---|---|
| Vehicle | 137.6 | 39-280 |
| PROLEUKIN ™ | 5.5 | 3-22 |
| Aldesleukin (Aggregates of the invention) | 4.3 | 1-12 |

1. The aldesleukin prepared by the method of this invention and used in this assay was freshly produced. In contrast, Table 3 shows the same assay performed with the aldesleukin prepared by the method of this invention after storage for 6 or 12 months at 2-8° C.

TABLE 3

Therapeutic activity of the aldesleukin/SDS aggregates obtained using the production method of the invention after 6 or 12 months of storage at 2-8° C. for 6 or 12 months. These results reinforce the idea that the liquid preparation of aldesleukin obtained by the method of the invention, is stable for at least a year.

| Treatment | metastases (mean) | range |
|---|---|---|
| Vehicle 6 month storage | 182 | 24-332 |
| Aldesleukin (Aggregates of the invention) 6 month storage | 8.4 | 0-35 |
| Vehicle 12 month storage | 123.2 | 12-156 |
| Aldesleukin (Aggregates of the invention) 12 month storage | 3.7 | 1-27 |

SEQUENCES

SEQ ID NO: 1
LENGTH: 132
PRT
ORGANISM: Artificial Sequence, mature des-alanyl-1 serine 125 variant of human interleukin-2
Pro Thr Ser Ser Ser Thr Lys Lys Thr Gln Leu Gln Leu Glu
His Leu Leu Leu Asp Leu Gln Met Ile Leu Asn Gly Ile
Asn Asn Tyr Lys Asn Pro Lys Leu Thr Arg Met Leu Thr
Phe Lys Phe Tyr Met Pro Lys Lys Ala Thr Glu Leu Lys
His Leu Gln Cys Leu Glu Glu Glu Leu Lys Pro Leu Glu
Glu Val Leu Asn Leu Ala Gln Ser Lys Asn Phe His Leu
Arg Pro Arg Asp Leu Ile Ser Asn Ile Asn Val Ile Val Leu
Glu Leu Lys Gly Ser Glu Thr Thr Phe Met Cys Glu Tyr
Ala Asp Glu Thr Ala Thr Ile Val Glu Phe Leu Asn Arg
Trp Ile Thr Phe Ser Gln Ser Ile Ile Ser Thr Leu Thr

REFERENCES

US Patent Documents

U.S. Pat. No. 4,604,377 Aug. 5, 1986

Other Patent Documents

EP 1 688 146 B1 18.07.2007
WO 2 017 068 031 A1 Apr. 27, 2017

OTHER PUBLICATIONS

1—Malek T R. The biology of interleukin-2. Annu Rev Immunol. (2008). 26:453-5 79. DOI: 10.1146/annurev.immunol.26.021607.090357
2—Dudley M E et al. Adoptive Cell Transfer Therapy Following NonMyeloablative but Lymphodepleting Chemotherapy for the Treatment of Patients With Refractory Metastatic Melanoma. Journal of Clinical Oncology. (2005). 23: 2346-57. DOI: 10.1200/JCO.2005.00.240
3—Langerman A, Callender G G, Nishimura M I. Retroviral transduction of peptide stimulated t cells can generate dual t cell receptor-expressing (bifunctional) t cells reactive with two defined antigens. Journal of Translational Medicine. (2004). 2:4-8. DOI: 10.1186/1479-5876-2-42
4—Magee M S, Snook A E. Challenges to chimeric antigen receptor (CAR)-T cell therapy for cancer. Discov Med. (2014). 18:265-71
5—Arenas-Ramirez N, Woytschak J, Boyman O. Interleukin-2: Biology, Design and Application. Trends Immunol. (2015). 36:763-777. DOI: 10.1016/j.it.2015.10.003
6—Hank J A, Surfus J, Gan, Albertini M, Lindstrom M, Schiller J H, Hotton K M, Khorsand M, Sondel P M. Distinct clinical and laboratory activity of two recombinant interleukin-2 preparations. Clin Cancer Res. 1999 5:281-9

What is claimed:

1. A method of producing aldesleukin suitable for the preparation of a composition comprising aldesleukin in a pharmaceutical aqueous vehicle, the method comprising: fermenting a bacterial cell transfected with an expression vector encoding an aldesleukin gene; disrupting the bacterial cell; collecting inclusion bodies containing aldesleukin; subjecting the inclusion bodies to dissolution by a detergent followed by oxidation and a first chromatography; diluting with an organic nitrile and subjecting to a second chromatography; subjecting the aldesleukin to diafiltration and sterilization, thereby producing aldesleukin aggregates in a pharmaceutical aqueous vehicle.

2. The method of claim 1, wherein the bacterial cell is an *Escherichia coli* bacterial cell.

3. The method of claim 1, wherein the detergent is sodium dodecyl sulfate (SDS).

4. The method of claim 1, wherein the oxidation is conducted with an oxidizing compound.

5. The method of claim 1, wherein the first chromatography is a ceramic hydroxyapatite chromatography.

6. The method of claim 1, wherein the second chromatography is a high performance liquid chromatography (HPLC).

7. The method of claim 6, wherein the HPLC is C4 column HPLC chromatography.

8. The method of claim 1, wherein the aldesleukin has a stable biological activity, at least for a year in the liquid composition, as measured in HT-2 cell culture.

9. The method of claim 1, wherein the aldesleukin is biologically active to be used in any cell therapy procedure involving cells expressing IL-2 receptors in their membranes.

10. The method of claim 1, wherein the aldesleukin is biologically active to be used in cell therapies involving NK and T cells in cell culture and any modified NK and T cells expressing IL-2 receptors in their membranes.

* * * * *